(12) United States Patent
Mitsumori

(10) Patent No.: US 6,447,447 B1
(45) Date of Patent: Sep. 10, 2002

(54) ENDOSCOPE WITH OBJECTIVE LENS DRIVE MECHANISM

(75) Inventor: Naotake Mitsumori, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 160 days.

(21) Appl. No.: 09/671,168

(22) Filed: Sep. 28, 2000

(30) Foreign Application Priority Data

Sep. 30, 1999 (JP) .......................................... 11-279261

(51) Int. Cl.[7] .............................................. A61B 1/00
(52) U.S. Cl. ....................... 600/167; 600/168; 600/129
(58) Field of Search ................................ 600/167, 168, 600/173, 160, 129, 106, 107; 359/694, 699, 700, 701, 823, 825, 826

(56) References Cited

U.S. PATENT DOCUMENTS

| | | | | |
|---|---|---|---|---|
| 5,191,879 A | * | 3/1993 | Krauter ........................ 359/823 |
| 5,231,473 A | * | 7/1993 | Kawamura et al. ......... 359/694 |
| 5,675,442 A | * | 10/1997 | Parks ........................... 359/368 |
| 5,832,317 A | * | 11/1998 | Shimizu ....................... 396/374 |
| 6,088,538 A | * | 7/2000 | Nakamura .................... 396/379 |
| 6,117,071 A | * | 9/2000 | Ito et al. ....................... 600/118 |
| 6,185,375 B1 | * | 2/2001 | Mikami ........................ 396/175 |

* cited by examiner

*Primary Examiner*—John P. Leubecker
(74) *Attorney, Agent, or Firm*—Oblon, Spivak, McClelland, Maier & Neustadt, P.C.

(57) ABSTRACT

An endoscope having an objective lens drive mechanism for an optical objective lens system, which is incorporated into a rigid tip end section of an elongated insertion instrument of the endoscope and provided with at least two movable lens groups which are movable in the direction of optical axis of the objective lens system. Ring members are connected to movable lens frames which support the respective movable lens groups. A cam pin is projected radially on the inner periphery of each ring member, while a cam shaft which is formed with a plural number of cam grooves on its circumferential surface is located in parallel relation with the optical objective lens system. The members are fitted on the cam shaft with the respective cam pins in engagement with the cam grooves. The cam shaft is rotated in forward and reverse directions by a drive means.

8 Claims, 9 Drawing Sheets

ENDOSCOPE WITH OBJECTIVE LENS DRIVE MECHANISM

BACKGROUND OF THE INVENTION

1. Field of the Art

This invention relates to an endoscope for use in medical examinations, and more particularly to an endoscope which is provided with an objective lens drive mechanism to move by remote control a plural number of lens groups of an optical objective lens system, which is incorporated into an observation window on a rigid tip end section of an elongated insertion instrument of the endoscope, for example, for adjustment of at least focal depth, image magnification rate or view field angle.

2. Prior Art

Generally, endoscopes which are in use for medical purposes are largely constituted by a manipulating head assembly to be gripped and manually operated by a hand of an operator, an elongated insertion instrument extended on the front side of the manipulating head assembly for insertion into a body cavity of a patient, and a universal cable which is led out from the manipulating head assembly and disconnectibly connected to a light source. For its functions, the elongated insertion instrument of an endoscope is successively constituted by, from its fore distal end, a rigid tip end section, an angle section and a flexible body portion. The flexible body portion occupies the major length of the elongated insertion instrument from a proximal end portion which is connected to the manipulating head assembly, and arranged to be bendable in arbitrary directions along a path of insertion. The rigid tip end section contains an illumination window or windows, an image pickup means, and an opening of a biopsy channel through which forceps or other instrument is introduced into a body cavity. The angle section is can be angularly bent by remote control from the manipulating head assembly, for turning the rigid tip end section into an arbitrary direction.

As mentioned above, the rigid tip end section contains at least an illumination window and an image pickup means. Located within the illumination window is a light emitting end of a light guide which is constituted by a bundle of fiber optics. The light guide is extended as far as the above-mentioned universal cable via the manipulating head assembly and disconnectibly connected to a light source. On the other hand, as the image pickup means, an optical objective lens system is fitted in an observation window on the rigid tip end section. In the case of an electronic endoscope, a solid-state image sensor device is located at the focus of the optical objective lens system. In the case of an optical endoscope, an image pickup end of a light guide, which is constituted by a bundle of fiber optics, is located at the focus of the optical objective lens system. A signal cable which is connected from the solid-state image sensor device or the image guide is passed through the insertion instrument along with the light guide and extended to the manipulating head assembly. An electronic endoscope which appears in the following description can be read and taken as an optical endoscope if a solid-state image sensor device and a signal cable is replaced by an image guide.

In addition to the above-mentioned component parts, an exit opening of a biopsy channel is provided on the rigid tip end section. Connected to the exit opening is a biopsy channel which is constituted by a flexible tube. Further, a wash nozzle is provided on the rigid tip end section to wash clean the observation window when contaminated. An air/water feed tube is connected to the wash nozzle. These biopsy channel and air/water feed tube are extended as far as the manipulating head assembly through the elongated insertion instrument of the endoscope.

As described above, an elongated insertion instrument of an endoscope is normally required to accommodate bundles of fiber optics, signal cable, biopsy channel and a number of feed tubes. In order to bend the angle section as described above, a pair of upper and lower operating wires or two pairs of vertical and horizontal operating wires are also passed through the insertion instrument. The fore ends of these operating wires are fixed either to the rigid tip end section or to a structural member in the proximity of the rigid tip end section. Within the angle section, the positions of the operating wires are restricted in circumferential direction. Further, the respective operating wires are extended as far as the manipulating head assembly through the flexible section of the endoscopic insertion instrument.

The optical objective lens system of the image pickup, which is normally constituted by a plural number of lenses, should preferably be capable of adjustments in focal depth, image magnification and view field angle, depending upon the position of an intracavitary portion to be examined or upon the purpose of examination. In this regard, it has been known to make part of the lenses of the optical objective lens system movable in the direction of optical axis for adjustments of focal depth, image magnification or view field angle.

As for drive means for moving a movable lens in the direction of optical axis of the objective lens system, there have been various proposals, including piezoelectric elements, shape memory alloys and artificial muscle. However, in actual applications, it has been the general practice to use a control cable for shifting the position of a movable lens or lenses by remote control. In such a case, the fore end of a control cables is connected to the movable lens, while the proximal end of the cable is extended into the manipulating head assembly in such a way that an operator can shift the position of a movable lens in the direction of optical axis by remote control from the head assembly. More particularly, a control cable of this sort is usually composed of a flexible sleeve and a number of transmission members which are fitted in the flexible tube. The transmission members are either in the form of push-pull type operating wires or in the form of a flexible rotation transmission shaft which is constituted by tightly wound coil tubes. In the case of push-pull wires, the fore end of operating wires are connected to a support member of a movable lens thereby to push or pull the movable lens. On the other hand, in the case of a flexible transmission shaft, a screw rod which is connected to the fore end of a flexible transmission shaft is engaged with a nut member which is provided fixedly on the part of a movable lens support member, for example, on a movable lens frame. Accordingly, in this case, a rotational movement of the flexible transmission shaft is translated into a linear movement of a movable lens. No matter whether the drive means employs the push-pull wires or a flexible transmission shaft, it can be arranged either as a manual drive or as a power drive having a motor or an actuator incorporated into a manipulating head assembly of an endoscope.

For instance, for varying an image magnification rate, it has been known to employ an objective lens system employing two lens groups, i.e., a variator lens and a compensator lens, which are movable in the direction of optical axis of the objective lens system independently of each other. In this instance, each one of the two lens groups is not necessarily composed of a plural number of lens elements, and can be composed of a single lens element. The two lens groups are moved in a different way from each other in distance, speed and direction. However, considering the smallness in diameter of the endoscopic insertion instrument, it has been found impossible to incorporate two independent drive means into the insertion instrument for the purpose of driving the two lens groups in different ways as mentioned above. In this connection, attempts have been made to provide movable lenses within a cam tube and to move a plural number of lenses concurrently in predetermined directions by rotating or linearly moving the cam tube, for example, as disclosed in Japanese Laid-Open Patent Application H11-42202. The drive mechanism according to this prior art employs a cam tube which is provided with a plural number of cam grooves in such a way as to circumvent lens tubes of an optical objective lens system. Lens frames of movable lenses are fitted in the cam tube, with pins on the lens frames in engagement with the cam grooves. The can tube is biased to protrude in the forward direction by the action of a biasing spring, while the cam tube can be pulled in the rearward direction along the circumferential surfaces of the lens tubes by pulling operating wires which are connected to the cam tube. Accordingly, by moving the cam tube in the forward or backward direction, the movable lenses are turned to shift their positions in the direction of optical axis.

An optical objective lens system which uses the above-mentioned prior art lens drive mechanism suffers from a drastic increase in diameter of an assembly of the objective lens system including the lens drive mechanism due to the use of the cam tube around lens tubes of the system in addition to a biasing spring and operating wires which are connected to the cam tube. Needless to say, a drastic increase in diameter is a detrimentally negative factor for an endoscopic insertion instrument.

Further, endoscopes are usually used for examination or observation within dark body cavities. Therefore, normally an illumination means is provided at the distal end of an endoscopic insertion instrument. However, since the insertion instrument is small in diameter, the illumination means is required to have a small aperture diameter and to project illumination light from an illumination window which is substantially in the form of a point light source. Therefore, an illumination lens is usually fitted in the illumination window to disperse the illumination light as much as possible. However, it has been found difficult to prevent variations in illumination level across a view field. Since a cam tube is fitted on lens tubes of an optical objective lens system of an image pickup, an illumination window or windows are necessarily located at a distant position from the image pickup. Consequently, at the time of observing an intracavitary portion in the proximity of a fore distal end of an endoscopic insertion instrument, there arises a problem that illumination light level drops conspicuously in a central region of an area under observation, failing to illuminate the whole view field sufficiently and uniformly.

A cam tube which is fitted on lens tubes needs to be driven from behind. Accordingly, operating wires and a biasing spring for the cam tube are located in positions behind the lens tubes. In this connection, in the case of an electronic endoscope, it is desirable for a solid-state image sensor device to have a broad image receiving surface area because the greater the number of its picture elements the higher becomes its resolution power. This means that the endoscopic insertion instrument should be provided with an image pickup means of a larger size including a solid-state image sensor device and its substrate board. In order to build in an image sensor device of a large size within increasing the outside diameter of the endoscopic insertion instrument, an image receiving surface of the solid-state image sensor device should preferably be disposed to face in the axial direction of the insertion instrument. For this purpose, it becomes necessary to bend a light path from an optical objective lens system through 90 degrees by the use of a prism which is located in a position behind lens tubes. Therefore, in case a cam tube is fitted on lens tubes, the prism may become an obstacle in connecting drive means to the cam tube and limit the size of the solid-state image sensor device to be used on the endoscopic insertion instrument.

SUMMARY OF THE INVENTION

In view of the difficulties as mentioned above, it is an object of the present invention to provide an endoscope with an objective lens drive mechanism which can shift positions of a plural number of movable lenses within a lens tube of an optical objective lens system smoothly in the direction of optical axis and without necessitating to increase the diameter of the lens tube to any conspicuous degree.

It is another object of the present invention to provide an endoscope with an objective lens drive mechanism which permits to locate illumination windows closely on opposite sides of an observation window of an image pickup portion, for illuminating a view filed of the image pickup substantially with a uniform light volume.

In accordance with the present invention, for achieving the above-stated objectives, there is provided an endoscope with an objective lens drive mechanism for an optical objective lens system mounted within an observation window on a rigid tip end section of an elongated insertion instrument of the endoscope, the optical objective lens system being composed of a plural number of lens groups including at least two movable lens groups to be moved in the direction of optical axis of the optical objective lens system, comprising: movable lens frames supporting the movable lens groups; ring members respectively connected to the movable lens frames and each provided with a radial cam pin on an inner peripheral side thereof; a cam shaft rotatably supported on the rigid tip end section in parallel relation with the optical objective lens system, and formed with cam grooves on circumferential surfaces thereof for engagement with cam pins on the ring members; and a drive means coupled with the cam shaft for rotationally driving same in forward and reverse directions.

In one specific form of the invention, for planting the radial cam pins on the respective ring members, a stepped through hole is formed in each ring member a cam pin is threaded into the stepped hole to project on the inner periphery of the ring member, with a flanged head portion of the cam pin in engagement with an outer larger diameter portion of the stepped hole. Preferably, each ring member is further provided with a resilient cover of substantially C-shape which is adapted to cover the stepped hole from outside. In case of an electronic endoscope, a large image pickup means is often used to obtain picture images of higher resolution. In order to incorporate a large image pickup means without increasing the outside diameter of the rigid tip end section of the endoscopic insertion instrument, an image receiving surface of a solid-state image sensor device has to be positioned in such a way as to face the optical axis of the objective lens system. For this purpose, a prism is employed to bend a light path from the objective lens system through 90 degrees. Further, arms members are connected between the ring members and the lens frames to offset the positions of the ring members to a sufficient degree relative to the movable lens frames, locating the cam shaft in a position out of interference with the prism of the objective lens system. As for a drive means for the cam shaft, there may be employed a control cable using a flexible rotation transmission shaft. Alternatively, in order to make the internal construction of the insertion instrument more compact, an electric motor may be coupled with the cam shaft. In this case, an output shaft of an electric motor may be coupled with an input portion of the cam shaft through transmission gears. In this regard, it is preferable to provide a predetermined clearance between the output shaft of an electric motor and the input portion of the cam shaft to ensure smooth transmission of rotation. Furthermore, the cam grooves on the cam shaft are preferred to have an inclination angle in the range of from 5 to 30 degrees.

The above and other objects, features and advantages of the present invention will become apparent from the following particular description of the invention, taken in conjunction with the accompanying drawings which show by way of example some preferred embodiments of the invention.

PREFERRED EMBODIMENTS OF THE INVENTION

Figure 1:
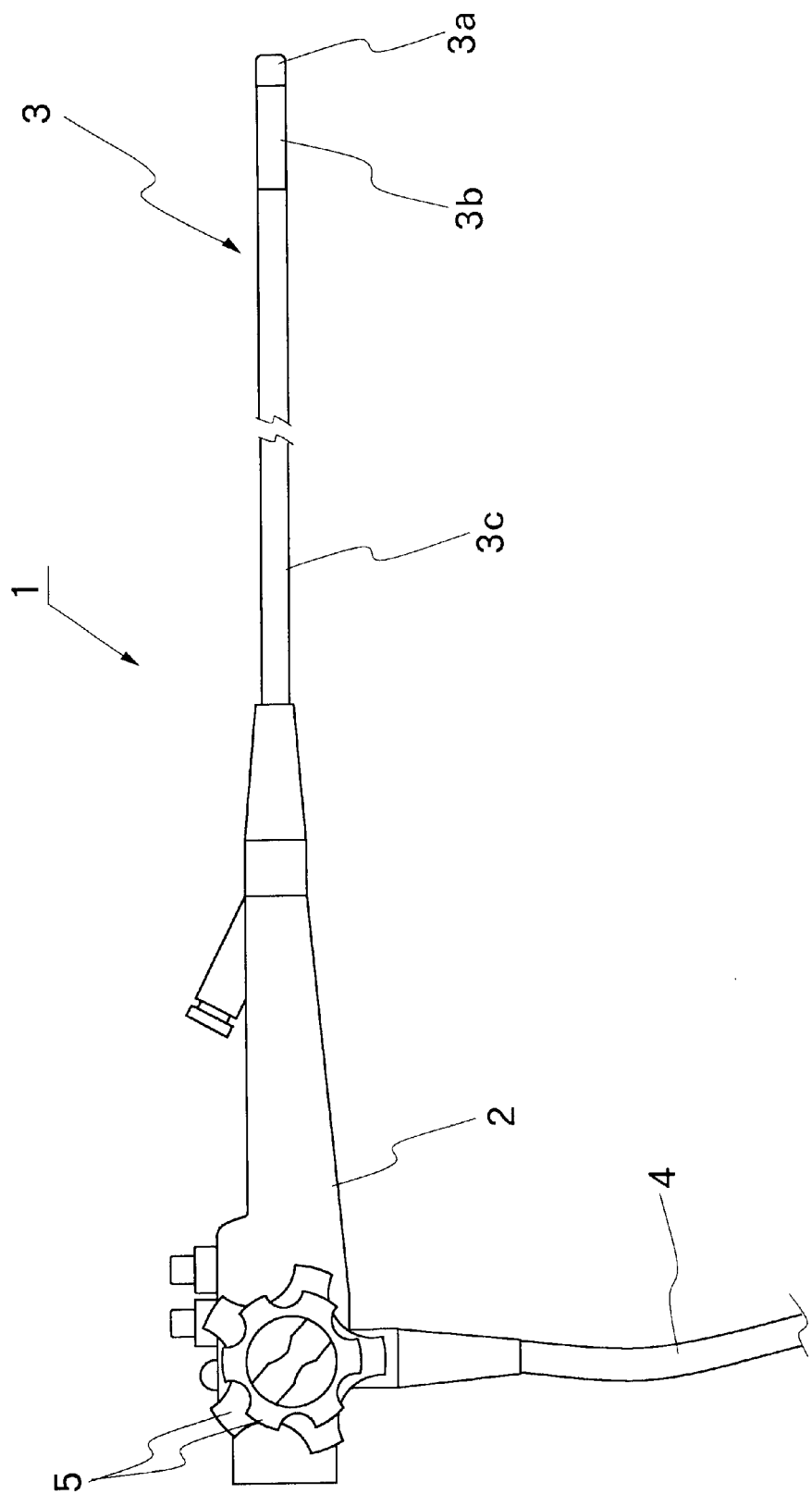
FIG. 1 is a schematic view of an endoscope embodying the present invention.
Figure 2:
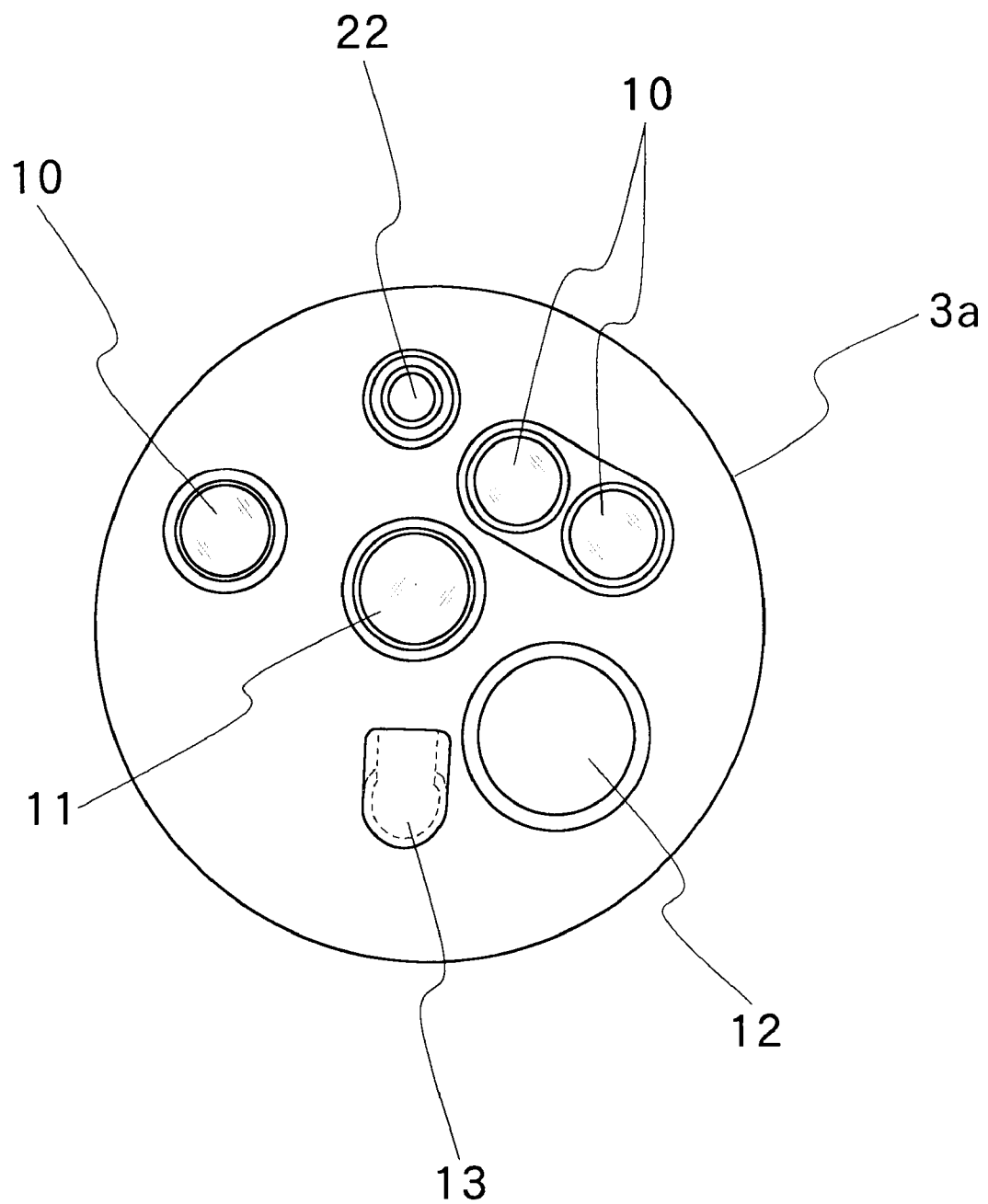
FIG. 2 is a schematic cross section of a distal end portion of an insertion instrument of the endoscope.

Referring first to FIG. 1, there is schematically shown the general layout of an endoscope. As seen in this figure, the endoscope 1 is largely constituted by a manipulating head assembly 2, an elongated insertion instrument 3 which is extended out on the front side of the manipulating head assembly 2 for insertion into a patient's body cavity or the like, and a universal cable which is led out on the rear side of the manipulating head assembly 2. For the functions required, the insertion instrument 3 is composed of, from its fore distal end, a rigid tip end section 3a, an angle section 3b and a flexible body section 3c.

The rigid tip end section 3a is housed in a casing of a rigid material and provided with illumination windows 10, an observation window 11, an outlet opening 12 of a biopsy channel, a washer nozzle 13 and so forth. In this instance, as shown in the drawing, the illumination windows 10 are normally provided at a plural number of positions on the opposite sides of the observation window 11. By manipulating an angle knob 5 which is provided on the manipulating head assembly 2, the angle section 3b can be bend in upward, downward, rightward and leftward directions to turn the rigid tip end section 3a into a desired direction. Further, the flexible body section 3c, which occupies a major portion of the entire length of the insertion instrument 3, is arranged to have a structure which has flexibility in bending directions along with resistance to crushing, so that it can be bent in arbitrary directions in a path of insertion which may contain turns and bends.

Figure 3:
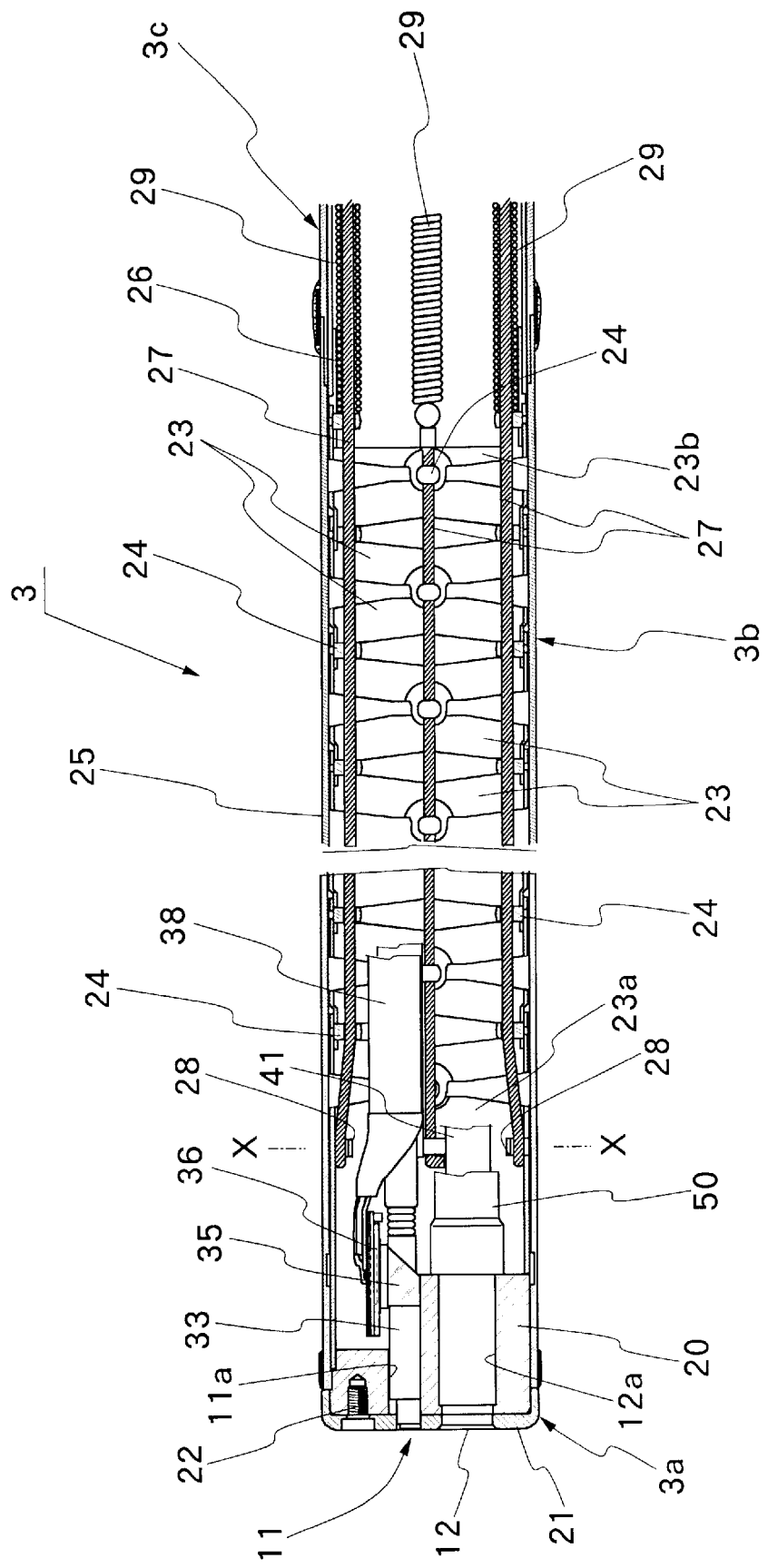
FIG. 3 is a schematic longitudinal section of the distal end portion of the endoscopic insertion instrument.

Shown in FIG. 3 is a cross section across a fore end portion of the insertion instrument 3. As seen in that figure, the rigid tip end section 3a is provided with a casing block 20 with a number of axial through holes or bores. Fitted on the fore end face of the casing block 20 is cap 21 which is securely fixed to the casing block 20 by means of stop screws 22. The angle section 3b is constituted by a series of angle rings 23 which are successively and connected one after another into the fashion of pivotally connected flexible nodal rings by the use of pivot pins 24. Fitted around the nodal ring structure of angle section 3b is a cover member 25, which is normally constituted by an inner layer of metal wire mesh and an outer skin layer of EPDM or the like. The foremost one of the angle rings 23, that is, an angle ring 23a in the foremost position is fixedly fitted on the core block 20 of the rigid tip end section 3a. On the other hand, the angle ring 23b on the side of the proximal end of the angle section 3a, that is, the angle ring 23b in the rearmost position is fixedly secured by welding or soldering to a connector ring 26 which connects the angle section 3a with the flexible body portion 3c. The flexible body section 3c is constituted by a metal coil tube, metal wire mesh which is fitted around the metal coil tube, and an outer skin layer formed further around the metal wire mesh. The construction of the flexible body portion 3c is omitted in the drawings since it is well known in the art.

As mentioned hereinbefore, the angle section 3b is bent into a desired direction by remote control from an angle knob 5 which is provided on the manipulating head assembly 2. For this purpose, two or four operating wires 27 are provided. In the angle section 3b, the operating wires 27 are passed through the pivot pins 24 in predetermined positions in the circumferential direction. The fore ends of the respective operating wires 27 are fixed to lanced stubs 28 which are provided on the foremost ring 23a. In the flexible body portion 3c, the operating wires 27 are passed through a tightly wound coil tube 29.

Figure 4:
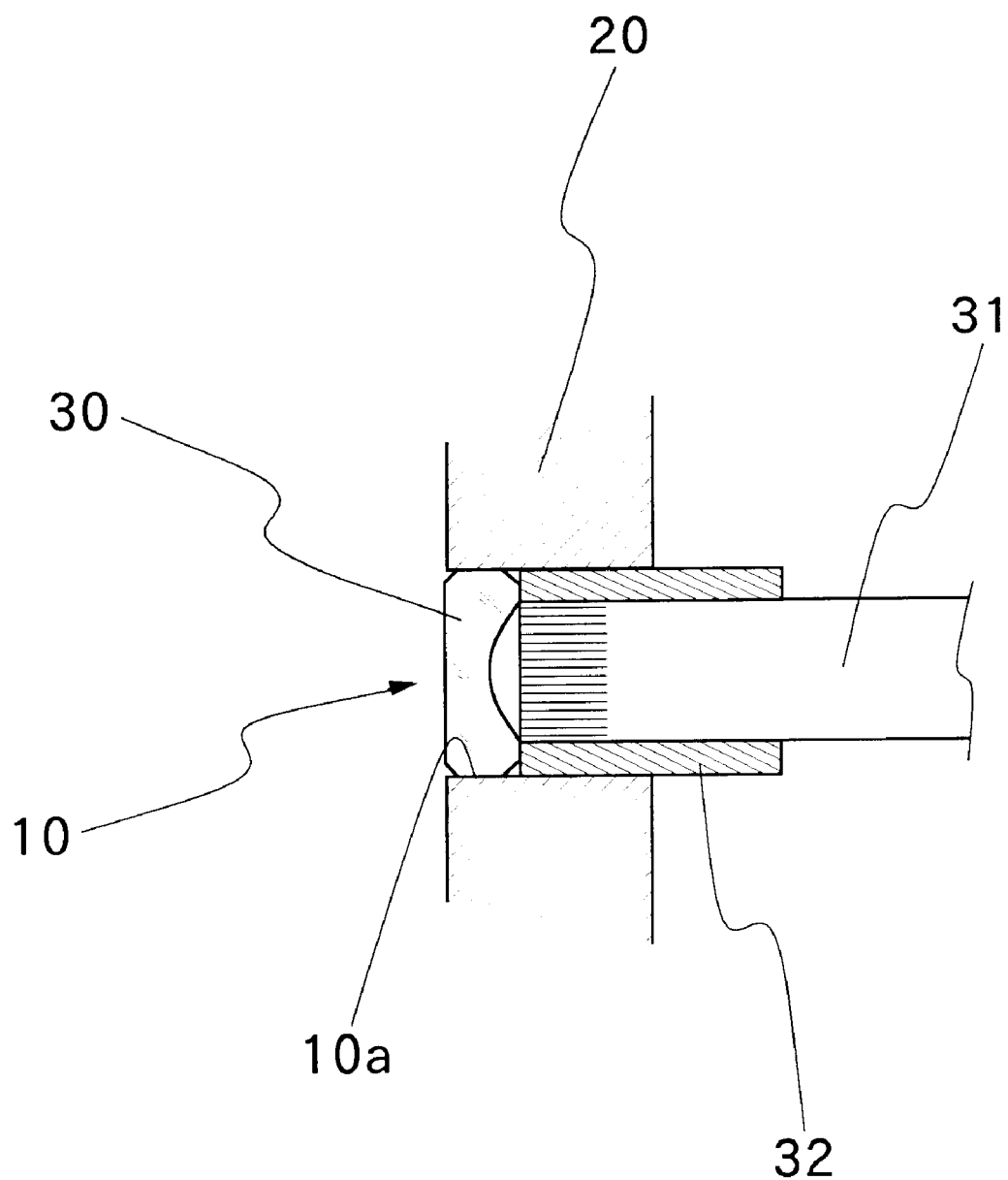
FIG. 4 is a schematic view of an illuminating section of the endoscopic insertion.

As shown in FIG. 4, the illumination windows 10 are each constituted by an opening 10a which is bored through the casing block 20, an illumination lens 30 which is fitted in the opening 10a, and a light guide 31. Illumination light which is emitted from the fore end of the light guide 31 is dispersed through the illumination lens 30 to irradiate broad areas. The light guide 31 is constituted by a bundle of a multitude of fine fiber optics. Except a fore end portion which is fitted in an frame ring 32 of the window opening 10a, the light guide 31 is loosely bundled in a freely flexible state by the use of a flexible tube or the like, and extended into the universal cable 4 through the insertion instrument 3 and via the manipulating head assembly 2.

Figure 5:
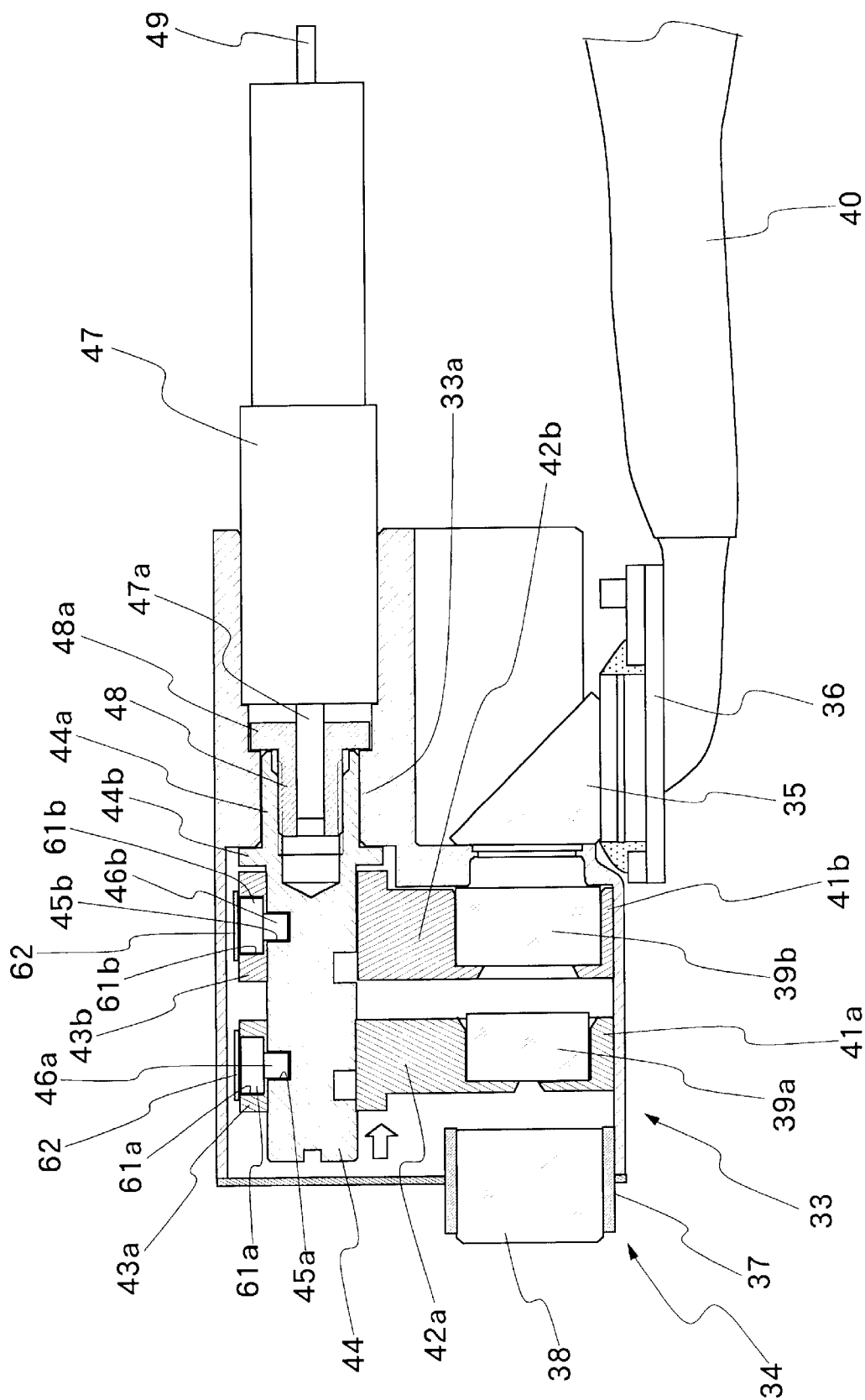
FIG. 5 is a schematic view of an image pickup section, showing movable lenses and a drive mechanism therefor.

As illustrated in FIG. 5, the observation window 11 includes an image pickup unit assembly 33 which is supported on an image pickup mount portion 11a, which is provided on the casing block 20 (FIG. 3). The image pickup unit assembly 33 includes an optical objective lens system 34, and a prism 35 which turns a light path from the optical objective lens system 34 through 90 degrees toward an image pickup means 36 which is located at the focus of the objective lens system 34. The optical objective lens system 34 is mounted in a lens retainer frame 37 which is provided fixedly on the image pickup unit assembly 33, and composed of a fixed lens group 38 consisting of one to several numbers of fixed lenses and movable lens groups 39a and 39b consisting of one to several number of movable lenses. The prism 35 is used to bend the optical axis of the optical objective lens system 34 by 90 degrees. The image pickup means 36 is constituted by a solid-state image sensor device which is located at the focus of the optical objective lens system 34, and a substrate wiring board for the image sensor device. Connected to the substrate are a large number of wires, which are bundled by the use of a flexible tube or by taping and extended as a signal cable 40 into the universal cable 4 through the insertion instrument 3 and the manipulating head assembly 2. Thus, the signal cable 40 as a whole is flexibly bendable.

The two lens groups 39a and 39b of the optical objective lens system 34 are movable back and forth in the direction of optical axis of the system. These movable lens groups 39a and 39b are mounted in movable lens frames 41a and 41b. Securely connected the movable lens frames 41a and 41b are arms 42a and 42b, respectively, which are formed with ring members 43a and 43b at the fore ends thereof. A cam shaft 44 is located in parallel relation with the optical axis of the optical objective lens system 34 and at a distant position from the latter. Cam grooves 45a and 45b are formed in circumferential directions around the circumferential surface of the cam shaft 44. Attached to the ring members 43a and 43b are cam pins 46a and 46b, respectively, for engagement with the cam grooves 45a and 45b. Accordingly, as the cam shaft 44 is rotated in forward and reverse directions, the cam pins 46a and 46b on the ring members 41a and 41b, which are in engagement with the cam grooves 45a and 45b, are put in forward and backward sliding or rolling movements in and along the cam grooves 45a and 45b. As a result, through the ring members 43a and 43b and the arms 42a and 42b, positions of the movable lens frames 39a and 39b are shifted forward or backward in the direction of the optical axis.

Figure 6:
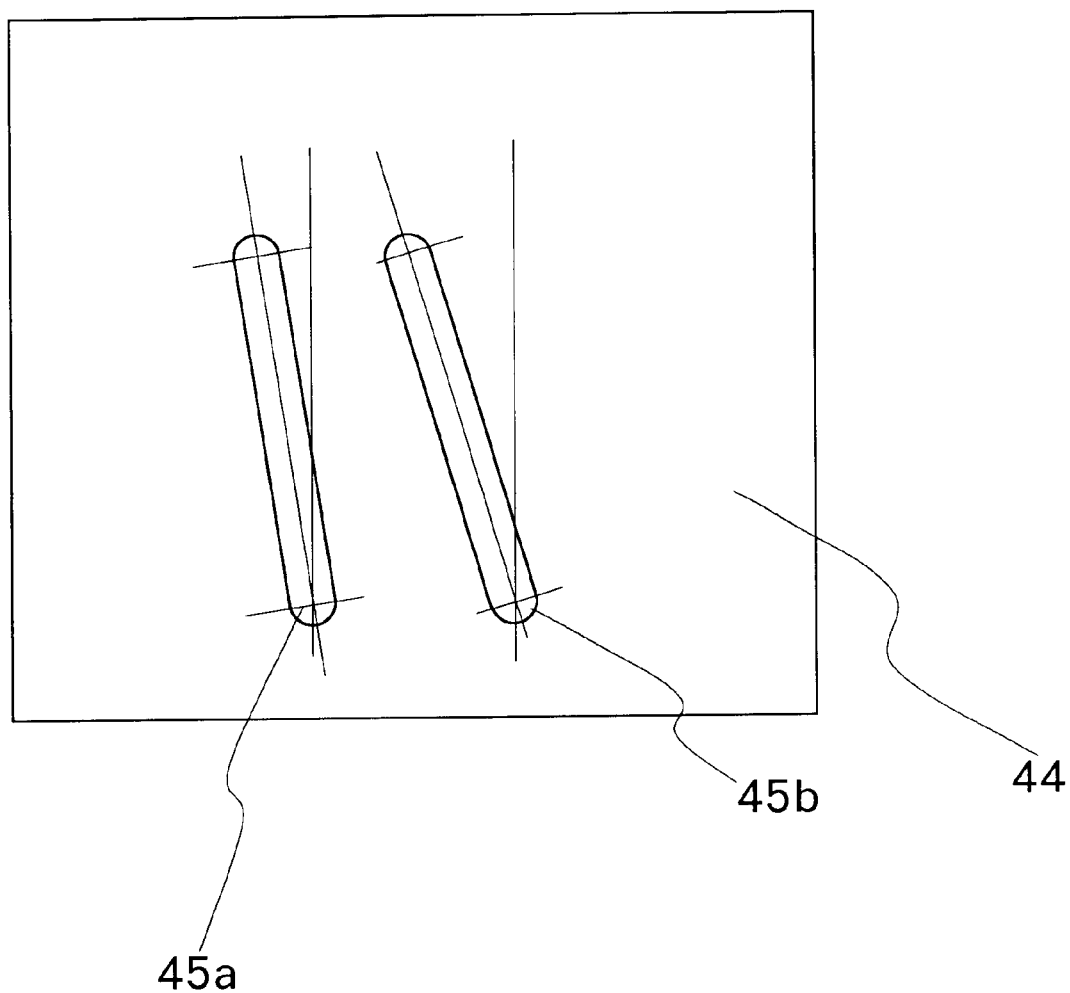
FIG. 6 is an expansion plan of a cam shaft.

As shown in FIG. 6, the two cam grooves 45a and 45b are formed in a predetermined length in the circumferential direction and angularly inclined relative to the longitudinal axis of the cam shaft 44. More specifically, the two cam grooves 45a and 45b are arranged with different inclination angles, so that, upon rotating the cam shaft 42, the movable lens frames 39a and 39b are put in different axial movements. In this instance, the smaller the inclination angles of the cam grooves 45a and 45, the smoother becomes the movements of the movable lens frames 39a and 39b. However, if the inclination angles are minimized to extremely small values, it becomes necessary to provide very lengthy cam grooves and to employ a cam shaft which is much larger in outside diameter. On the contrary, in case the cam grooves 45a and 45b are formed with greater inclination angles, a greater driving force is required to move the movable lens groups 39a and 39b respectively along the cam grooves 45a and 45b. Therefore, it is preferable that the inclination angles of the cam grooves 45a and 45b fall in a range of from 5 degree to 30 degrees and are differentiated from each other by a necessary angle for putting the two movable lens groups in differentiated axial movements.

In order to rotationally drive the cam shaft 44, a reversible electric motor 47 is mounted on the image pickup unit assembly 33. Output shaft 47a of the electric motor 47 is coupled with a transmission shaft 48 through key or spline coupling. Further, provided at the proximal end of the cam shaft 44 is a coupling extension 44a. The transmission shaft 48 connected to the cam shaft 44 through threaded engagement with the coupling extension 44a. A flange 48a is provided at the proximal end of the transmission shaft 48, while a flange 44b is provided on the front side of the coupling extension 44a. A support wall portion 33a of the image pickup unit assembly 33 is firmly griped between these flanges 48a and 44b. As a consequence, the cam shaft 44 is rotatable but restricted of movements in other directions. Further, indicated at 49 in the drawing is a cable which is led out from the electric motor 47.

Figure 7:
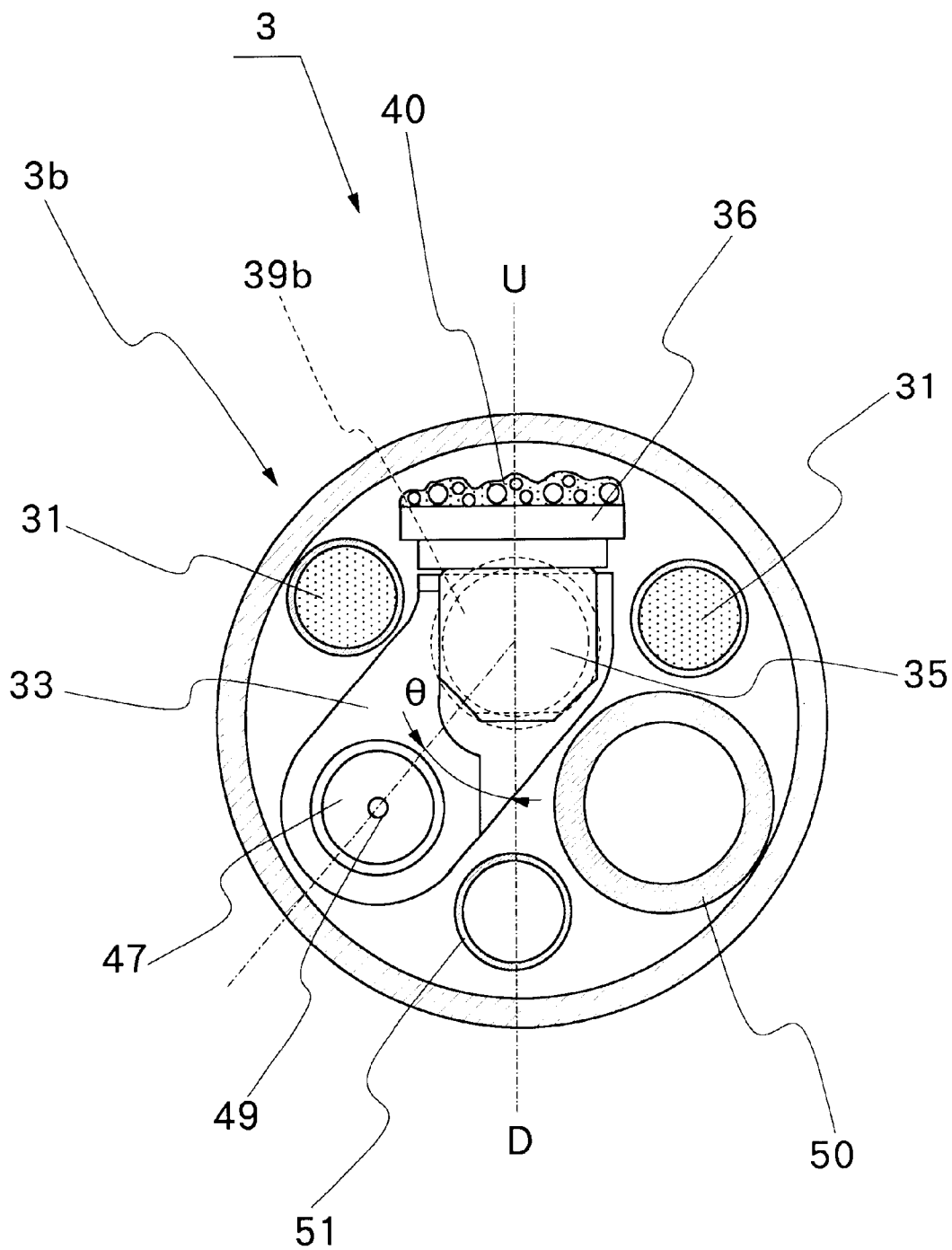
FIG. 7 is a schematic section taken in the direction of X—X of FIG. 3.
Figure 8:
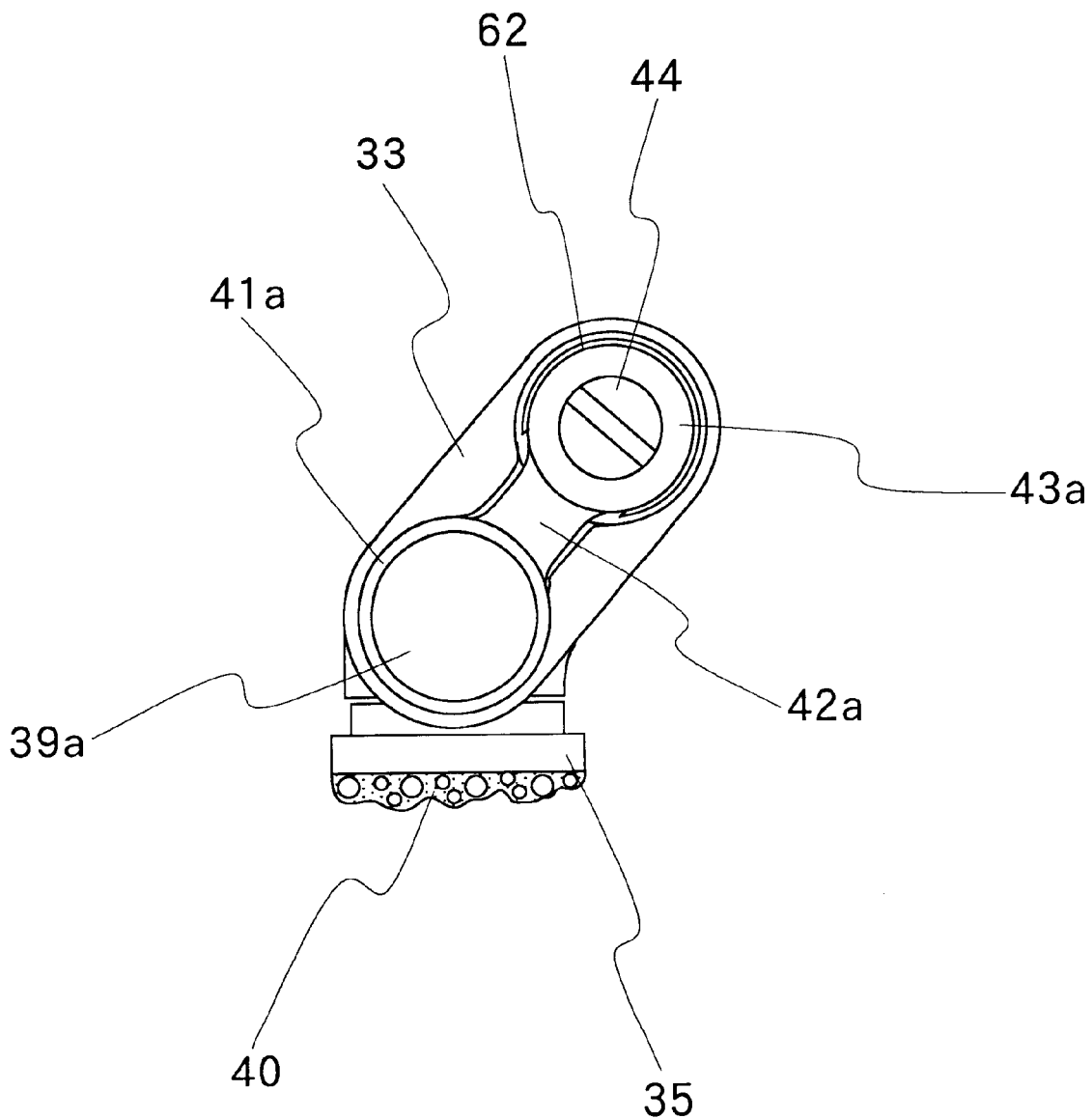
FIG. 8 is a schematic view taken in the direction of an arrow in FIG. 5.

As shown in FIGS. 7 and 8, the optical objective lens system 34 inside the observation window 11 is located along and substantially on the upper side of a longitudinal center line of the casing block 20 in the rigid tip end section 3a. On the other hand, the cam shaft 44, which moves the movable lens groups 39a and 39b of the optical objective lens system 34 in the direction of the optical axis, as well as the driving electric motor 47 is offset in an obliquely lower position. Accordingly, the arms 42a and 42b are obliquely inclined by a predetermined angle θ (FIG. 7) relative to a vertical center line U-D. Located on the opposite side of the vertical center line U-D, i.e., on the side away from the arms 42a and 42b, is a biopsy instrument channel 50 which is connected to the biopsy instrument exit opening 12. Further, located closely to the vertical center line U-D is an air/water feed tube 41 which is connected to the washing nozzle 13. On the other hand, the light guides 31 which are connected to the illumination windows 10 are located in upper positions within the rigid tip end section 3b.

The cam pins 46a and 46b may be provided integrally with the ring members 43a 43b which are fitted on the cam shaft 44. However, alternatively, the cam pins 46a and 46b may be set in stepped bores 60a and 60b which are provided on the ring members 43a and 43b as shown in FIG. 5. In this case, the cam pins 46a and 46b are provided with flanged heads 61a and 61b which fit in larger diameter portions of the stepped bores 60a and 60b. Thus, the cam pins 46a and 46b are passed through smaller diameter portions of the stepped bores 60a and 60b to engage with the cam grooves 45a and 45b, respectively. Resilient retainer rings 62 are fitted in the ring members 43a and 43b in such a way as to cover the stepped bores 60a and 60b from outside, thereby preventing dislocation of the cam pins 46a and 46b out of the stepped bores 60a and 60b.

For example, magnification rate of an image under observation by an endoscope can be varied by way of the movable lens groups 39a and 39b of the optical objective lens system 34 in the manner as follows. Firstly, the insertion instrument 3 of the endoscope is introduced into a body cavity, sending the rigid tip end section 3a to a site of examination or observation. Under illumination by light rays from the illumination window, an image of an intracavitary site is taken by the optical objective lens system 34 through the observation window 11 and displayed on a monitor screen to check the conditions of the intracavitary site under observation. During the observation or examination, by bending or flexing the angle section 3b by remote control from the manipulating head assembly, the rigid tip end section 3a of the insertion instrument 3 can be turned into an arbitrary direction to shift the observation view field toward a spot of particular interest. In this case, images are taken by the optical objective lens system 34 at a low magnification rate.

For a closer examination, the magnification rate is increased upon detecting a suspicious or diseased spot in the course of an initial examination or observation. For this purpose, a button on the manipulating head assembly 2 is operated to rotate the electric motor 44 in the forward or reverse direction. As a result, the cam shaft 44 is rotated, causing the cam pins 46a and 46b to move long the cam grooves 45a and 45b, respectively, and the movable lens frames 41a and 41b of the movable lens groups 39a and 39b are moved independently of each other in the direction of the optical axis to increase the image magnification rate. Accordingly, although the observation view filed is limited to some extent, a close-up image of a spot of particular interest can be obtained for a closer examination or observation.

The cam shaft 44, which serves as a drive means fro the respective movable lens groups 39a and 39b as described above, is supported by the arms 42a and 42b in a distant position from the optical axis of the optical objective lens system 34 and in parallel relation with the optical axis. Therefore, there are no possibilities of the prism 35, which is located behind the optical objective lens system 34 for turn the light path from the objective lens system by 90 degrees, interfering with the cam shaft 44 and the driving electric motor 47 for the cam shaft 44. Accordingly, it becomes possible to locate the image pickup means 36 in a position under the optical objective lens system 34, namely, substantially at the center of the insertion instrument 3, with its image receiving surface area disposed parallel with the optical axis of the objective lens system 34. This means that a solid-state image sensor device having a broad image receiving area can be employed as the image pickup means 36 to display sharp images of high resolution on a monitor screen, which would improve the accuracy of examination or observation of intracavitary sites or the like to a considerable degree.

Besides, although the image pickup unit assembly 33, including the optical objective lens system 34, requires an extra mounting space in an obliquely downward direction for the arms 42a and 42b which are connected to the movable lens frames 41a and 41b, it can be thinned down to a smaller width. Therefore, the light guides 31 as well as the illumination windows 10 which receive light emitting ends of the light guides 31 can be located closely on the opposite lateral sides of the observation window 11 of the optical objective lens system 34. The close positioning of the illumination windows is effective for suppressing unevenness of illumination light distribution across an observation view field, especially for taking extremely clear images of a subject by preventing uneven illumination light distribution in center regions of an observation view field when the subject is located at a close distance of from 1 to several centimeters from the observation window 11.

Further, the interposition of the arms 42a and 42b between the movable lens frames 41a and 41b and the ring members 43a and 43b makes it possible to locate the cam shaft 44 arbitrarily in a distant position from the optical axis of the object lens system 34. If the lengths of the arms 42a and 42b are increased, however, a bending load will be exerted through engaging portions of the cam pins 46a and 46b and the cam grooves 45a and 45b. In this connection, since the cam shaft 44, which is connected to an output shaft of the electric motor 47 at its proximal end through the transmission shaft 48, is left free at its fore end in the fashion of a cantilever. Accordingly, by the loads which are exerted on engaging portions of the cam pins 46a and 46b and the cam grooves 45a and 45b, a bending force can be exerted on the coupling portion between the transmission shaft 48 and the output shaft of the electric motor 47 to hinder smooth power transmission between these members.

Axial strokes of the movable lens groups 39a and 39b depend on the length and angle of the cam grooves 45a and 45b, respectively. In a case where the movable lens groups 39a and 39b are used to provide a variable image magnification, normally these lens groups are moved between a low magnification position and a high magnification position. For instance, it is desirable to use the objective lens system in a low magnification rate at the time of examining or observing a broad area of an intracavitary site, and in a high magnification rate when it becomes necessary to close up a spot or region of particular interest for closer examination. Accordingly, it suffices for the lens drive to be able to position the two movable lens groups 39a and 39b accurately at the opposite stroke ends which are determined by the cam grooves 45a and 45b.

Figure 9:
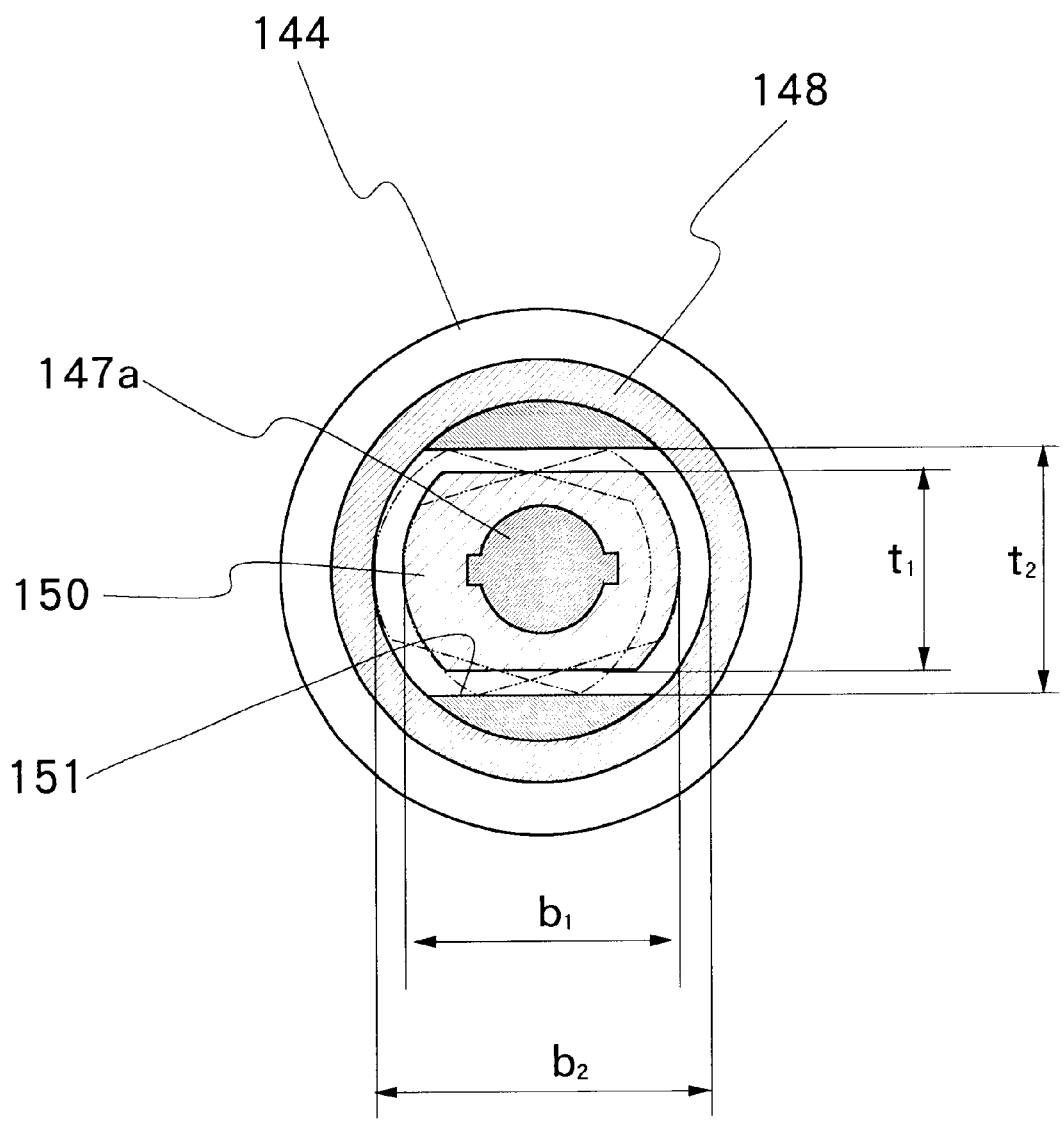
FIG. 9 is a schematic view showing relations between a transmission shaft and a cam shaft in a modification according to the present invention.

In this connection, as shown in FIG. 9, a transmission shaft 148 and an output shaft 147a of an electric motor can be coupled with each other through a clearance of a predetermined width. More specifically, as seen in that figure, a flat coupling member 150 is fixed on an end portion of the output shaft 147a while a coupling recess 151 is formed into the proximal end face of the transmission shaft 148 for loose fitting engagement with the flattened coupling member 150 on the part of the output shaft 147a. More particularly, the coupling recess 151 has height $t_2$ and width $b_2$ which are larger than height $t_1$ and width $b_1$ of the flattened coupling member 151, respectively. Accordingly, clearances of $t_2-t_1$ and $b_2-b_1$ are provided on the upper and/or lower side and on the right and/or left side of the flat coupling member 150, providing a play between the flat coupling member 150 and the coupling recess 151 in the rotational direction. When the flat coupling member 150 is tilted within the coupling recess 151 as indicated by an imaginary line in the same figure, power is transmitted from the output shaft 147a to the transmission shaft 148 to rotate the cam shaft 144. When coupled in this manner, rotation can be transmitted from the output shaft 147a to the transmission shaft 148 even if there is a certain degree of misalignment between these parts. However, the existence of a clearance may make it difficult to hold the movable lens groups in position as soon as they come to a stroke end position. This problem can be solved by continuously apply the load of the electric motor at the stroke end position. Alternatively, a biasing spring may be interposed between the flat coupling member 150 and the coupling recess 141 in such a manner as to bias the coupling member 150 in one rotational direction relative to the coupling recess 151. In this case, for example, it becomes unnecessary to continuously apply the load of the electric motor at one position on the side of low image magnification.

The optical objective lens system in the above-described embodiment is provided with two movable lens groups. However, needless to say, the present invention can be applied to endoscopic objective lens systems with three or more movable lens groups. Further, for the cam shaft, there may be employed a rotational drive means other than the electric motor 47, for example, there may be employed a control cable having tightly wound coil tubes fitted in a flexible sleeve.

What is claimed is:

1. An endoscope with an objective lens drive mechanism for an optical objective lens system mounted within an observation window on a rigid tip end section of an elongated insertion instrument of said endoscope, said optical objective lens system being composed of a plural number of lens groups including at least two movable lens groups to be moved in the direction of an optical axis of said optical objective lens system, comprising:

movable lens frames supporting said movable lens groups;

ring members respectively connected to said movable lens frames and each provided with a radial cam pin on an inner peripheral side thereof;

a cam shaft rotatably supported on said rigid tip end section in parallel relation with said optical objective lens system, and formed with cam grooves on circumferential surfaces thereof for engagement with cam pins on said ring members; and a drive means coupled with said cam shaft for rotationally driving said cam shaft in forward and reverse directions.

2. An endoscope with an objective lens drive mechanism as defined in claim 1, wherein said ring members are provided with a stepped through hole having an outer larger diameter portion and an inner smaller diameter portion, and said cam pin is threaded in said stepped hole, with a flanged head portion of said cam pin in engagement with said outer larger diameter portion of said stepped hole.

3. An endoscope with an objective lens drive mechanism as defined in claim 2, wherein said ring members are further provided with a resilient cover of substantially C-shape adapted to cover said stepped hole from outside.

4. An endoscope with an objective lens drive mechanism as defined in claim 1, further comprising a prism located behind said optical objective lens system to bend a light path through 90 degrees toward a image sensor means which is located at the focus of said optical objective lens system, and arms connected between said movable lens frames and said ring members to locate said cam shaft in a position out of interference with said prism.

5. An endoscope with an objective lens drive mechanism as defined in claim 1, wherein said drive means of said cam shaft is constituted by an electric motor coupled with said cam shaft.

6. An endoscope with an objective lens drive mechanism as defined in claim 5, wherein an output portion of said electric motor and an input portion of said cam shaft are coupled with each other through a predetermined clearance, providing a play between said input and output portions in a rotational direction.

7. An endoscope with an objective lens drive mechanism as defined in claim 1, wherein said cam grooves on said cam shaft are inclined at an angle in a range from 5 and 30 degrees.

8. An endoscope with an objective lens drive mechanism as defined in claim 1, wherein said rigid tip end section of said insertion instrument further comprises illumination windows on the opposite sides of said observation window along with an exit opening of a biopsy channel located under said observation window, and said arms are extended in an obliquely downward direction away from said exit opening of said biopsy channel from a position between said illumination windows.

* * * * *